United States Patent
Jindal et al.

(10) Patent No.: US 11,147,273 B2
(45) Date of Patent: Oct. 19, 2021

(54) DUAL ACTIVE PARASITICIDAL GRANULE COMPOSITIONS, METHODS AND USES THEREOF

(71) Applicant: BOEHRINGER INGELHEIM ANIMAL HEALTH USA INC., Duluth, GA (US)

(72) Inventors: Kour Chand Jindal, Mumbai (IN); Jian Han, East Tamaki (NZ); Kim Agnew, North Ryde (AU)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 16/017,880

(22) Filed: Jun. 25, 2018

(65) Prior Publication Data

US 2018/0368406 A1 Dec. 27, 2018

Related U.S. Application Data

(60) Provisional application No. 62/524,746, filed on Jun. 26, 2017.

(51) Int. Cl.
| | | |
|---|---|---|
| *A01N 43/90* | (2006.01) | |
| *A01N 25/14* | (2006.01) | |
| *A01N 43/68* | (2006.01) | |

(52) U.S. Cl.
CPC .............. *A01N 43/68* (2013.01); *A01N 25/14* (2013.01); *A01N 43/90* (2013.01)

(58) Field of Classification Search
CPC ......... A01N 43/68; A01N 25/14; A01N 43/90
See application file for complete search history.

(56) References Cited

U.S. PATENT DOCUMENTS

| | | | |
|---|---|---|---|
| 3,627,885 A | 12/1971 | Rondelet | |
| 4,048,268 A | 9/1977 | Ludwig | |
| 4,597,969 A | 7/1986 | Maxfield | |
| 7,396,819 B2 | 7/2008 | Burke | |
| 7,582,612 B2 | 9/2009 | Ahn | |
| 7,671,034 B2 | 3/2010 | Freehauf | |
| 8,835,397 B2 | 9/2014 | Nanjan | |
| 2005/0064032 A1* | 3/2005 | Lowe | A61K 9/0007 424/468 |
| 2009/0214608 A1 | 8/2009 | Monin | |

FOREIGN PATENT DOCUMENTS

| | | | |
|---|---|---|---|
| CN | 1297680 A | 6/2001 | |
| CN | 1308861 A | 8/2001 | |
| CN | 101380008 A | 3/2009 | |
| CN | 101416635 A | 4/2009 | |
| CN | 101524075 A | 9/2009 | |
| CN | 102972421 A | 3/2013 | |
| CN | 103385242 A | 11/2013 | |
| CN | 103843803 A | 6/2014 | |
| CN | 106359422 A | 2/2017 | |
| CN | 106879609 A | 6/2017 | |
| CN | 107372516 A | 11/2017 | |
| CN | 107372541 A | 11/2017 | |
| CN | 107787977 A | 3/2018 | |
| EP | 0659341 B1 | 10/1999 | |
| EP | 2005/094210 B1 | 10/2005 | |
| EP | 1863468 A1 * | 12/2007 | ........... A61K 9/0017 |
| GB | 2220856 A | 1/1990 | |
| WO | 9925187 A2 | 5/1999 | |
| WO | 9925188 A2 | 5/1999 | |
| WO | 0002453 A1 | 1/2000 | |
| WO | 0137667 A1 | 5/2001 | |
| WO | 2005063015 A1 | 7/2005 | |
| WO | 2008/072987 A1 | 6/2008 | |
| WO | 2015/118468 A1 | 1/2011 | |
| WO | 2011/027333 A1 | 3/2011 | |
| WO | 2011123773 A1 | 10/2011 | |
| WO | 2015118468 A1 | 8/2015 | |

OTHER PUBLICATIONS

Piedmont Animal Health, Flynexx Granules, internet download http://www.piedmontanimalhealth.com/flynexx/ (downloaded on Aug. 29, 2018).

Piedmont Animal Health Flynexx Granules 2% Cyromazine Material Safety Data Sheet.

Hoko Chemicals, Hokoex, Internet download https://www.hoko.com/473/515.html (downloaded on Aug. 29, 2018).

Sandeman, et al.,Control of the sheep blowfly in Australia and New Zealand—are we there yet?, International Journal for Parasitology,Oct. 15, 2014, pp. 879-891, vol. 44, Issue 12, Elsevier, Amsterdam, Netherlands.

Rolim, et al., Preformulation study of ivermectin raw material, Journal of Thermal Analysis and Calorimetry, Apr. 2015, pp. 807-816, vol. 120, Issue 1, Springer Nature, Switzerland.

\* cited by examiner

*Primary Examiner* — Marcos L Sznaidman
*Assistant Examiner* — Rayna Rodriguez
(74) *Attorney, Agent, or Firm* — Katrina Bergbauer

(57) ABSTRACT

The present invention encompasses a stabilized parasiticidal granule composition comprising a macrocyclic lactone compound and an insect growth regulator. The invention also encompasses methods of making and methods of using the granule for treating, controlling or preventing parasitic infestation or parasitic infection in an animal.

16 Claims, No Drawings

DUAL ACTIVE PARASITICIDAL GRANULE COMPOSITIONS, METHODS AND USES THEREOF

CROSS REFERENCE TO RELATED APPLICATIONS

This application claims the benefit of priority to U.S. Provisional Application No. 62/524,746, filed Jun. 26, 2017, and incorporated herein in its entirety.

FIELD OF THE INVENTION

The invention relates to stable parasiticidal granules and methods for treatment of animals using the granules, wherein the granules comprise a macrocyclic lactone, such as ivermectin, and an insect growth regulator, such as cyromazine.

BACKGROUND

Parasitic infestations/infections are a serious and ongoing concern in human and animal health. Parasites include ectoparasites that are insects, such as flies, mosquitoes, fleas and lice, and arachnids, such as ticks and mites. Parasites also include endoparasites which are filiariae and other worms. Sheep and other domesticated livestock are subject to infestation by a number of endoparasitic roundworms, tapeworms and flukes, as well as ectoparasites such as lice, blow fly, ticks, head fly, keds and mites (e.g. in "sheep scab"). A major pest in sheep farming is the sheep blow fly, whose larvae is a parasite that can cause significant suffering and loss of production in infected sheep. At certain times of the year when blow flies are active, the adult blow fly will lay eggs on sheep. When the eggs hatch, the larval stage will then feed on the flesh of the infected sheep, causing what is known as blow fly strike or sheep myiasis.

Over the years, a wide variety of treatments have been used to control and prevent infestation by blowfly (Sandeman et al. Int. J. Parasitol. 44 (2014), 879-891). The first of these included organophosphates, such as diazinon, which has fallen into disfavour due to blowfly larvae resistance and because of occupational health and safety concern for operators applying the chemicals. Another class of chemicals used for blow fly treatment or prevention are the Insect Growth Regulators (IGRs). Compounds belonging to the IGR group are well known to the practitioner and represent a wide range of different chemical classes, many of which are indexed by their international common name in The Pesticide Manual: A World Compendium, 16$^{th}$ edition, 2012, Ed. C. MacBean, Great Britain. In general, IGRs act by interfering with the development or growth of the insect pests, and are described, for example, in U.S. Pat. Nos. 3,748,356; 3,818,047; 4,225,598; 4,798,837; 4,751,225, EP 0179022 or U.K. 2 140 010 as well as U.S. Pat. Nos. 6,096,329 and 6,685,954 (both owned by Merial Inc., Duluth, Ga.).

Some IGR compounds act by blocking the development of immature stages (eggs and larvae) into adult stages, which includes the so-called chitin synthesis inhibitors "CSIs" that inhibit the synthesis of chitin, a major component of the insect exoskeleton. Insects treated with CSIs are unable to synthesize new cuticle and are therefore unable to successfully moult into the next stage of their life cycle. CSI's include chlorfluazuron, diflubenzuron, fluazuron, flucycloxuron, flufenoxuron, hexaflumuron, lufenuron, tebufenozide, teflubenzuron, triflumuron, novaluron, 1-(2,6-difluorobenzoyl)-3-(2-fluoro-4-(1,1,2,2-tetrafluoroethoxy)phenylurea and 1-(2,6-difluorobenzoyl)-3-(2-fluoro-4-trifluoromethyl) phenylurea. Diflubenzuron, was registered as a sheep blow-fly larvacide until resistance became so severe that flystrike protection claims were removed from some product labels.

Cyromazine is an IGR that has achieved widespread use as a means to control blow fly larvae. It is applied to sheep in the form of a dip, pour on or a spray on. In the dip form, animals are completely saturated with the formulation, whereas with the pour on and spray formulation, only those areas of the animal likely to be infected by blow fly larvae are treated. Granular cyromazine products, such as Hokoex® (Hokochemie GmbH, Berne, Switzerland) and Flynexx™ (Piedmont Animal Health, Greensboro, N.C.) are marketed for use in the dry form or for mixing with water for control of fly larvae in manure piles and in animal rearing facilities. The pyrimidine insect development inhibitor, dicyclanil, is another IGR compound that is used in commercial liquid blowfly strike products (e.g. Clik®, Novartis Animal Health). The mechanism of action for dicyclanil is thought to be related to interference with the process of insect chitin deposition, as opposed to inhibition of chitin synthesis. Cyromazine may act similarly.

Some compounds in the IGR class mimic juvenile insect hormones, which force the insect to remain in a juvenile state. Methoprene, including (S)-methoprene, and pyriproxyfen are examples of juvenile hormone mimics. Others include azadirachtin, diofenolan, fenoxycarb, hydroprene, kinoprene, tetrahydroazadirachtin, and 4-chloro-2-(2-chloro-2-methyl-propyl)-5-(6-iodo-3-pyridylmethoxy) pyridizine-3(2H)-one.

In general use it is important that veterinary formulations are stable for a reasonable period of time and are able to withstand a variety of climatic and temperature conditions. Typically fly-strike treatments are pour-on or spray-on formulations for topical administration. With spray-on or pour-on applications, aqueous based formulations are preferred. This type of formulation allows an even spread and accurate dosing of the active ingredient around the infected areas of the animal. However, the poor water solubility of many actives is a situation that may hamper the preparation of stable aqueous compositions.

One strategy that has been pursued for improving the water solubility of cyromazine is the production of certain salts in situ. Cyromazine has the ability to form mono and di salts with various organic and inorganic acids because it exhibits weak basic characteristics. However, many cyromazine salts are also poorly soluble in water, with only a few having solubilities in excess of 100 g/L in water at 20° C. Some examples exhibiting improved solubility are the acetate, lactate, sulphate, and tartrate salts of cyromazine. However, when subjected to temperatures below 20° C., their water solubility is reduced further. This reduced solubility may result in the formation of crystals which tend not to re-dissolve when the formulation returns to an ambient temperature. In another approach, WO2008/072987 describes solutions of cyromazine in polyethylene glycol solvent systems which are physically stable at low temperatures and are capable of being diluted with water before use.

For good efficacy against a variety of animal pests and ease of use, it may be desirable to combine different classes of compounds in a single composition. For instance, it may be of interest to combine one or more insect growth regulator compound with one or more other veterinary agent, including but not limited to, acaricides, anthelmintics, antiparasitics, insecticides and insect repellents. Veterinary agents well-known in the art are listed, for example in Plumb's Veterinary Drug Handbook, 5th Edition, ed. Donald C. Plumb, Blackwell Publishing, (2005) and The Merck Veterinary Manual, 9th Edition, (January 2005).

Macrocyclic lactones are a class of pesticide that has activity against a number of internal and external parasites. The macrocyclic lactones include, but are not limited to, avermectins, such as abamectin, dimadectin, doramectin, emamectin, eprinomectin, ivermectin, latidectin, lepimectin and selamectin; and milbemycins, such as milbemectin, milbemycin D, milbemycin oxime, moxidectin and nemadectin. Also included are the 5-oxo and 5-oxime derivatives of said avermectins and milbemycins. For an overview of avermectins, see "Ivermectin and Abamectin," W. C. Campbell, ed., Springer-Verlag, New York (1989).

The macrocyclic lactone, ivermectin, is an active ingredient in a number of veterinary products on the market. IVOMEC® Drench for Sheep and IVOMEC® Liquid with Selenium (Merial, Inc.) are ivermectin solutions that provide treatment and control of gastrointestinal roundworms, lungworms, nasal bots and itchmite of sheep. Ivermectin is also effective against flystrike, and is the active, for instance, in a concentrate for topical use against blowfly strike (Coopers®Paramax® Multi-Purpose Concentrate for Sheep, Intervet Australia).

A well-known formulation challenge with ivermectin is its instability in water. Ivermectin is also susceptible to acid and base catalyzed decomposition, oxidative decomposition, and photodegradation. Decomposition due to interaction with other ingredients in a composition is another legitimate concern. Specific strategies that are employed to mitigate degradative drug loss in ivermectin tablets (e.g. Heartgard® tablets, Merial Inc.) include low levels of ivermectin inclusion (around 0.03% of the tablet weight) and good drug distribution within the excipient mix.

A stabilized formulation of an avermectin feed premix having extended shelf life is described in U.S. Pat. No. 7,671,034 to Freehauf, wherein the premix contains an acid stabilizer, such as citric acid, which decreases or prevents formation of acid/base catalyzed degradates of the avermectin. Avermectins and milbemycins are susceptible to both acid and base catalyzed degradation. The macrocyclic lactone of all avermectins has at carbon 13 an α-L-oleandrosyl-α-L-oleandrosyloxy substituent which is a 2-deoxy sugar glycoside; and as such it is relatively sensitive to acid hydrolysis or alcoholysis. A solution of ivermectin in methanol containing a strong acid such as 1% sulfuric acid readily gives a good yield of the aglycone after 16 to 24 hours at room temperature. These procedures readily yield the monosaccharides of ivermectin and Avermectin B1 and the aglycone of ivermectin.

Also, the two degradates, 2-epimer and the $\Delta^{2,3}$ isomer of avermectin and milbemycins, are formed in the presence of a base. For example, decrease in ivermectin as the active ingredient in premix formulations is caused by formation of ivermectin degradate 2-epimer, which is a product of base catalyzed degradation in ivermectin.

U.S. Pat. Nos. 7,396,819 and 7,852,612 describe solid formulations wherein avermectin particles are coated with polyethylene glycol, which protects and isolates avermectin from other actives in the formulation. U.S. Pat. No. 8,835,397 describes a method for producing a macrocyclic lactone tablet containing a non-aqueous solvent, preferably benzyl alcohol, and a co-solvent, preferably a propylene glycol solvent. The solvents and co-solvents act together to increase the overall stability of the product.

Cyrazin KO is a concentrated suspension of cyromazine and ivermectin (50% cyromazine/1.5% ivermectin). The concentrate is intended to be diluted with water, such as a 500 fold dilution, to provide a jetting liquid for protecting coarse wool sheep against strikes by common blowflies including *Lucilia cuprina, Lucilia sericata* and *Calliphora stygia*.

In view of the problems mentioned above, there is a need for veterinary compositions with improved stability and ease of use for protecting animals. In this regard, a stable and easy to use IGR/macrocyclic lactone composition would be of great benefit.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

In a first aspect, the invention is a stable veterinary granule that contains two types of pesticidal actives: at least one macrocyclic lactone, and at least one insect growth regulator. In one embodiment, the present invention provides a parasiticidal veterinary granule comprising at least one macrocyclic lactone compound, at least one insect growth regulator (IGR), at least one surfactant excipient, and at least one diluent excipient, wherein the granule remains stable and pharmaceutically active for at least 6 months, and said granule, when mixed in water, forms a parasiticidally effective liquid composition. In one preferred embodiment, the macrocyclic lactone is ivermectin and the IGR is cyromazine. In a particularly preferred embodiment, the granule remains stable and pharmaceutically active for at least 2 years.

In a second aspect, the invention provides a method for treating, controlling, or preventing an ectoparasite infestation and/or an endoparasite infection in an animal comprising administering to an animal a solution formed by mixing with water a granule according to the first aspect. In one embodiment, the aqueous solution formed with the granule is administered to an animal topically. In one preferred embodiment, the invention provides a method for treating, controlling or preventing fly strike and louse infestations in sheep.

In a third aspect, the invention provides a method of making a granule according to the first aspect. A fourth aspect of the invention is the use of a granule of the first aspect in the manufacture of a medicament for the therapeutic and/or prophylactic treatment of an animal against an ectoparasite infestation and/or an endoparasite infection.

These and other aspects and embodiments are disclosed or are obvious from and encompassed by, the following Detailed Description.

DETAILED DESCRIPTION OF THE INVENTION

In a first aspect, the invention is a stable veterinary granule that contains two types of pesticidal actives: a macrocyclic lactone, and an insect growth regulator.

In one embodiment, the present invention provides a parasiticidal veterinary granule comprising at least one macrocyclic lactone compound, at least one insect growth regulator (IGR), at least one surfactant excipient, and at least one diluent excipient, wherein the granule remains stable and pharmaceutically active for at least 6 months, and said granule, when mixed in water, forms a parasiticidally effective liquid composition.

The term "macrocyclic lactone" as used herein includes both naturally occurring and synthetic or semi-synthetic avermectin and milbemycin compounds.

The macrocyclic lactones that may be used in the compositions of the invention include, but are not limited to, the naturally produced avermectins (e.g. including the components designated as A1a, A1b, A2a, A2b, B1a, B1b, B2a and B2b) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin A3, milbemycin A4, milbemycin oxime, moxidectin and nemadectin. Also included are the 5-oxo and 5-oxime derivatives of said avermectins and milbemycins.

In one embodiment, the compositions of the invention may comprise an effective amount of at least one of abamectin, dimadectin, doramectin, emamectin, eprinomectin, ivermectin, latidectin, lepimectin, selamectin, milbemectin, milbemycin D, milbemycin A3, milbemycin A4, milbemycin oxime, moxidectin or nemadectin, or a combination thereof. In another embodiment, the invention provides a veterinary composition comprising an effective amount of at least one of abamectin, emamectin, eprinomectin, ivermectin, doramectin or selamectin, or a combination thereof. In still another embodiment, the veterinary compositions of the invention comprise an effective amount of at least one of ivermectin, milbemectin, milbemycin oxime or moxidectin, or a combination thereof.

The insect growth regulators (IGRs) are well known in the art and represent a wide range of different chemical classes. IGR compounds are advantageously included in the compositions of the invention to provide superior efficacy against ectoparasites. These compounds all act by interfering with the development or growth of the insect pests. For example, some IGR compounds act by blocking the development of immature stages (eggs and larvae) into adult stages, or by inhibiting the synthesis of chitin. Some compounds in the IGR class mimic juvenile hormones. Insect growth regulators are described, for example, in U.S. Pat. Nos. 3,748,356; 3,818,047; 4,225,598; 4,798,837; 4,751,225, EP 0 179 022 or U.K. 2 140 010 as well as U.S. Pat. Nos. 6,096,329 and 6,685,954 (all incorporated herein by reference). Examples of IGRs suitable for use in the compositions of the invention include, but are not limited to, azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3-(2H)-one, cyromazine, chlorfluazuron, diflubenzuron, fluazuron, flucycloxuron, flufenoxuron, hexaflumuron, lufenuron, tebufenozide, teflubenzuron, triflumuron, novaluron, 1-(2,6-difluorobenzoyl)-3-(2-fluoro-4-trifluoromethyl)phenylurea, 1-(2,6-difluorobenzoyl)-3-(2-fluoro-4-trifluoromethyl)phenylurea, 1-(2,6-difluorobenzoyl)-3-(2-fluoro-4-(1,1,2,2-tetrafluoroethoxy)phenylurea and 1-(2,6-difluorobenzoyl)-3-(2-fluoro-4-trifluoromethyl)phenylurea.

In some embodiments of the invention, the insect growth regulator is selected from cyromazine, dicyclanil, diflubenzuron, fluazuron, formamidines, hydroprene, lufenuron, methoprene, novaluron, pyriproxyfen, triflumuron, and mixtures thereof. In some embodiments, the insect growth regulator is cyromazine, dicyclanil, or a combination thereof. In some embodiments, the compositions of the invention preferably comprise cyromazine.

In one embodiment, the macrocyclic lactone includes at least one avermectin. In another embodiment, the macrocyclic lactone includes at least one milbemycin. In one embodiment, the macrocyclic lactone includes at least ivermectin and the IGR includes at least cyromazine.

In certain embodiments of the invention, the granules of the instant invention remain stable and pharmaceutically active for at least 3 months, at least 4 months or at least 5 months. In another embodiment, the granules of the instant invention remain stable and pharmaceutically active for at least 6 months. A stable and pharmaceutically active granule meets or exceeds chemical and/or physical performance criteria (or specifications) for a period of time. The stability period wherein the granule meets or exceeds the specification may be designated as the shelf life of the granule. The performance criteria may be set by a regulatory agency, or may be set by an organization as an internal quality standard specific to that organization. In particularly preferred embodiments, the sum of the degradation products of the macrocyclic lactone or ivermectin in the inventive granules are below 5%. In one embodiment, the sum of the degradation products of the macrocyclic lactone or ivermectin in the inventive granules are below 5% for at least 3 months, at least 4 months or at least 5 months. In another embodiment, the sum of the degradation products of the macrocyclic lactone or ivermectin in the inventive granules are below 5% for at least 6 months.

In another embodiment, the sum of the macrocyclic lactone or ivermectin degradation products is less than 3% for at least 3 months, for at least 4 months or for at least 5 months. In one embodiment, the sum of the macrocyclic lactone or ivermectin degradation products is less than 3%. In a particularly preferred embodiment, the sum of the degradation products RRT 1.19 and RRT1.26 is <2.7% w/w, wherein the degradation products RRT 1.19 and RRT1.26 are designations for ivermectin degradation products having an HPLC retention time=1.19 and 1.26 minutes. In certain embodiments, the sum of the degradation products RRT 1.19 and RRT1.26 is <2.7% w/w for at least 3 months, at least 4 months or at least 5 months. In another embodiment, the sum of the degradation products RRT 1.19 and RRT1.26 is <2.7% w/w for at least 6 months. In one embodiment of the invention, the granules remain stable and pharmaceutically active for at least 1 year. In a particularly preferred embodiment of the invention, the granules remain stable and pharmaceutically active for at least 2 years. In some embodiments of the invention, the diluent and surfactant excipients contained in the granules are effective to prevent the macrocyclic lactone or ivermectin from degrading such that the sum of the degradation products RRT 1.19 and RRT1.26 are <2.7% w/w.

In one embodiment, the diluent and surfactant excipients contained in the granules are effective to prevent the macrocyclic lactone or ivermectin from degrading such that at least 87% of the formulated amount of macrocyclic lactone or ivermectin is retained for at least 6 months, or for at least 1 year when stored at 30° C., when stored at 40° C., or when stored at 30° C. and at 40° C. for at least 6 months, or for at least 1 year. In certain embodiments, at least 90%, or at least 92%, or at least 95%, or at least 96%, or at least 97%, or at least 98%, or at least 99% of the formulated amount of macrocyclic lactone or ivermectin is retained for at least 6 months, or is retained for at least one year storage at 30° C., at 40° C., or at 30° C. and at 40° C. In certain embodiments, at least 95%, at least 96%, at least 97%, at least 98% or at least 99% of the formulated amount of insect growth regulator or cyromazine is retained for at least six months or at least one year when the granule is stored at 30° C., at 40° C., or at 30° C. and at 40° C.

In some embodiments, the stability of the granules of the invention is such that the macrocyclic lactone and insect growth regulator concentration are each at least 95% of the amount formulated after 6 months, 12 months, 18 months, 24 months, 36 months, 48 months, or more than 48 months after manufacturing. In a preferred embodiment, the concentration of macrocyclic lactone and/or insect growth regulator is at least 96% of the amount formulated 6, 12, 18, 24, 36, 48, or more than 48 months after manufacture. In other embodiments the amount of the macrocyclic lactone and/or insect growth regulator is at least 97%, 98%, 99%, or more than 99% of the amount formulated 6, 12, 18, 24, 36, 48, or more than 48 months after manufacture.

In some embodiments of the parasiticidal granules according to the invention, at least 99% of the formulated amount of an insect growth regulator and at least 95% of the formulated amount of a macrocyclic lactone is retained for at least 12 months.

In some embodiments of the parasiticidal granules according to the invention, at least 99% of the formulated amount of cyromazine and at least 95% of the formulated amount of ivermectin is retained for at least 12 months. Retention of at least 99% cyromazine and retention of at least 95% ivermectin is an indication that the granule is stable and effect for at least 12 months under normal storage conditions, such as storage at 30° C., and that the granule has at least a 12 month shelf life. In some embodiments of the parasiticidal granules according to the invention, at least 99% of the formulated amount of cyromazine and at least 95% of the formulated amount of ivermectin is retained for at least 12 months at 30° C., at 40° C., or at 30° C. and at 40° C. In certain embodiments, the granule remains stable and pharmaceutically active for at least 2 years or for at least 3 years.

As would be understood by one skilled in the art, when the particle size of the granule is reduced, it may be considered to be a powder. Accordingly, the instant invention encompasses powder compositions of at least one macrocyclic lactone compound, at least one insect growth regulator (IGR), at least one surfactant excipient, and at least one diluent excipient, wherein the powder remains stable and pharmaceutically active for at least 6 months, and said powder, when mixed in water, forms a parasiticidally effective liquid composition.

The invention also encompasses methods of making granules according to the first aspect and use of granules of the first aspect in the manufacture of a medicament for the therapeutic and/or prophylactic treatment of an animal against an ectoparasite infestation and/or an endoparasite infection. The invention also encompasses methods for treating, controlling, or preventing an ectoparasite infestation and/or an endoparasite infection in an animal. According to one embodiment, the invention is a method of treating, controlling, or preventing fly strike or louse infestation (*Bovicola ovis*) in sheep comprising administering to said sheep a solution formed by mixing with water a granule of the first aspect.

Certain embodiments of the invention are described in the examples and claims herein.

As would be understood by one skilled in the art, the inventive granule formulations may contain antioxidant stabilizers, preservatives, and/or pH stabilizers. The compounds are well known in the formulation art. Tableting manufacture is described, for example, in the technical papers available on the internet from excipient manufacturer DFE pharma (www.dfepharma.com) such as "Introduction to tableting by wet granulation". Wet granulation is a tablet manufacturing process which can be used to manufacture the granules of the invention.

The antioxidant stabilizer BHT (butylated hydroxyl toluene) is important for the chemical stability of avermectins. Other antioxidants known in the art may be used in the inventive formulations, including, but not limited to, alpha tocopherol and tocopherol derivatives, ascorbic acid, ascorbyl palmitate, BHA (butylated hydroxyl anisole), fumaric acid, malic acid, monothioglycerol, propyl gallate, sodium ascorbate, sodium metabisulphite, and TBHQ (tert-butylhydroquinone) also could be used. Representative preservatives are parabens, including methylparaben and/or propylparaben. Other preservatives known to one skilled in the art include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycinate, tris, glutamic acid/glutamates and sodium carbonate.

Excipients that are diluents and binders are also contemplated for the inventive granules. Excipients for tableting are contemplated for the instant invention and are described, for example, in "Biomedical and Pharmaceutical Polymers", ed. Labarre et al. (2011). Diluents provide bulk to a composition and also may impart particular properties to the composition, such as helping with dissolution, compactability, and cohesiveness of the formulation. Binders are used in the formulation of solid products to assist in holding the active and inactive ingredients together in a cohesive mix.

In some embodiments, the diluent excipient in the granules comprises one or more water soluble sugars, such as sucrose, dextrose, xylitol, sorbitol, maltitol, lactose, mannitol, and fructose. In one embodiment, the diluent excipient preferably comprises lactose, mannitol, or a mixture thereof.

In some embodiments, the granules comprise at least one polymer excipient. In some embodiments, the granules comprise at least one polymer excipient that is a water miscible binder.

In some embodiments, the granules contain one or more water miscible binders including, but not limited to water soluble sugars, Povidone, cellulose derivatives, gelatin, polyethylene glycols, polyvinyl alcohol, gelatin, starch, etc.

In some embodiments, the polymer excipient preferably comprises polyvinylpyrrolidone, hydroxypropylmethylcellulose, or a mixture thereof.

According to certain embodiments of the invention, the surfactant excipient in the granule comprises at least one surfactant. Examples of surfactants that may be used in the inventive compositions include, but are not limited to, glyceryl monooleate, polyoxyethylene sorbitan fatty acid esters, sorbitan esters including sorbitan monooleate (Span®️ 20), polyvinyl alcohol, polysorbates including polysorbate 20 and polysorbate 80, d-α-tocopheryl polyethylene glycol 1000 succinate (TPGS), sodium lauryl sulfate, co-polymers of ethylene oxide and propylene oxide (e.g. poloxamers such as LUTROL®️ F87 and the like), polyethylene glycol castor oil derivatives including polyoxyl 35 castor oil (Cremophor®️ EL), polyoxyl 40 hydrogenated castor oil (Cremophor®️ RH 40), polyoxyl 60 hydrogenated castor oil (Cremophor®️ RH60), propylene glycol monolaurate (LAUROGLYCOL®️), glyceride esters including glycerol caprylate/caprate (CAPMUL®️ MCM), polyglycolized glycerides (GELUCIRE®️), PEG 300 caprylic/capric glycerides (Softigen®️ 767), PEG 400 caprylic/capric glycerides (Labrasol®️), PEG 300 oleic glycerides (Labrafil®️ M-1944CS), PEG 300 linoleic glycerides (Labrafil®️ M-2125CS), polyethylene glycol stearates and polyethylene glycol hydroxy stearates including polyoxyl 8 stearate (PEG 400 monostearate), polyoxyl 40 stearate (PEG 1750 monostearate, and the like. Polyethylene glycol stearates (synonyms include macrogol stearates, polyoxylstearates, polyoxyethylene stearates, ethoxylated stearates; CAS No. 9004-99-3, 9005-08-7) are mixtures of mono- and distearate esters of mixed polyoxyethylene polymers. Polyethylene glycol hydroxystearate is a mixture of mono- and diesters of hydroxystearic acid with polyethylene glycols. One polyethylene glycol hydroxystearate that may be used in the compositions is polyethylene glycol 12-hydroxystearate. In another embodiment, the compositions may include the surfactant polyethylene glycol 15 12-hydroxystearate (Solutol®️ HS 15 from BASF), a mixture of mono- and diesters of 12-hydroxystearic acid with 15 moles of ethylene oxide. Again, these compounds, as well as their amounts are well known in the art. In another embodiment of the invention, the compositions may include polyoxyl 35 castor oil (Cremophor®️ EL) as a surfactant. In other embodiments, the compositions may include polyoxyl 40 hydrogenated castor oil (Cremophor®️ RH 40) or polyoxyl 60 hydrogenated castor oil (Cremophor®️ RH60) as surfactants. The compositions of the invention may also include a combination of surfactants.

In some embodiments, surfactants include:

(a) anionic surfactants such as alkaline stearates, in particular sodium, potassium or ammonium stearate; calcium stearate; triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, (b) cationic surfactants such as water-soluble quaternary ammonium salts of formula N+R'R"R'"R"",Y⁻ in which the radicals R are optionally hydroxylated hydrocarbon radicals and Y⁻ is an anion of a strong acid such as the halide, sulphate and sulphonate anions; cetyltrimetylammonium bromide is among the cationic surfactants which can be used, (c) amine salts of formula N⁺R'R"XR'" in which the radicals R are optionally hydroxylated hydrocarbon radicals; octadecylamine hydrochloride is among the cationic surfactants which can be used, (d) nonionic surfactants such as optionally polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (e) amphoteric surfactants such as substituted lauryl compounds of betaine, and (f) a mixture of at least two, a mixture of at least three, or a mixture of more than three surfactants, or types of surfactants.

In some embodiments of the invention, the surfactant comprises a cationic surfactant, such as cetrimide; a non-ionic surfactant, such as a polysorbate or a poloxamer; or an anionic, surfactant such as sodium lauryl sulphate or docusate.

In one embodiment, the surfactant excipient comprises a cationic surfactant. In one embodiment, the surfactant excipient comprises at least one quaternary ammonium compound. In one embodiment, the surfactant excipient comprises ≤20% (w/w) cetrimide.

In yet another embodiment, the surfactant excipient comprises about 5 to about 25% of a polysorbate, such as polysorbate 20, polysorbate 60, polysorbate 65, polysorbate 80, and polysorbate 85 (w/w). In one embodiment, the surfactant excipient preferably comprises polysorbate 80, and in one embodiment, the surfactant preferably comprises about 5 to about 25% polysorbate 80.

In a first aspect, the invention is a parasiticidal veterinary granule comprising
(a) at least one a macrocyclic lactone compound;
(b) at least one insect growth regulator (IGR);
(c) at least one surfactant excipient; and
(d) at least one diluent excipient,
wherein said granule remains stable and pharmaceutically active for at least 6 months, and said granule, when mixed in water, forms a parasiticidally effective liquid composition.

In one embodiment of the invention according to the first aspect, the macrocyclic lactone compound comprises ivermectin. In one embodiment, the macrocyclic lactone consists of ivermectin. In certain embodiments, the amount of macrocyclic lactone or ivermectin is about 0.5% to about 2.0% (w/w). In certain embodiments, the amount of macrocyclic lactone or ivermectin is about 0.7 to about 1.7% (w/w). In certain embodiments, the amount of macrocyclic lactone or ivermectin is about 1.0 to about 2.0% (w/w). In certain embodiments, the amount of macrocyclic lactone or ivermectin is about 1.5% (w/w).

In certain embodiments of the invention according to the first aspect, the insect growth regulator (IGR) is selected from the group consisting of cyromazine, dicyclanil, diflubenzuron, fluazuron, formamidines, hydroprene, lufenuron, methoprene, novaluron, pyriproxyfen, triflumuron, and mixtures thereof. In some embodiments, the IGR comprises cyromazine, dicyclanil, or a combination thereof. In one embodiment, the IGR comprises cyromazine.

In some embodiments, the granule of the first aspect comprises about 1 to about 99% (w/w) of one or more IGRs. In one embodiment, the amount of IGRs is about 25 to about 60% (w/w). In one embodiment, the amount of IGRs is about 1 to about 60% (w/w). In one embodiment, the amount of IGRs is about 25 to about 55% (w/w). In other embodiments, the amount of IGR is about 45 to about 55% (w/w). In one embodiment, the amount of IGR is about 50% (w/w). In certain embodiments according to the first aspect of the invention, the IGR comprises about 1 to about 99% (w/w) cyromazine, about 1 to about 75% (w/w) cyromazine, about 25 to about 75% (w/w) cyromazine, about 25 to about 60% (w/w) cyromazine, about 1 to about 60% (w/w) cyromazine, about 25 to about 55% cyromazine, (w/w), about 45 to about 55% (w/w) cyromazine, or about 50% (w/w) cyromazine.

In some embodiments according to the first aspect of the invention, the granules comprise at least one macrocyclic lactone, at least one insect growth regulator, a surfactant excipient comprising ≤20% (w/w) cetrimide, and a diluent excipient comprising lactose, mannitol, or a mixture thereof. In some embodiments, the macrocyclic lactone comprises ivermectin. In some embodiments, the insect growth regulator comprises cyromazine.

In some embodiments according to the first aspect of the invention, the granules comprise about 0.5 to about 3.0% (w/w) of a macrocyclic lactone, about 25 to about 75% (w/w) of at least one insect growth regulator, a surfactant excipient comprising about 1 to about 20% (w/w) cetrimide, and a diluent excipient comprising lactose, mannitol, or a mixture thereof. In some embodiments, the macrocyclic lactone comprises ivermectin. In some embodiments, the insect growth regulator comprises cyromazine. In some embodiments, the granule further comprises a water miscible polymeric binder.

In some embodiments according to the first aspect of the invention, the granules comprise at least one macrocyclic lactone, at least one insect growth regulator, a surfactant excipient comprising about 5 to about 25% (w/w) polysorbate 20, polysorbate 60, polysorbate 65, polysorbate 80, or polysorbate 85, and a diluent excipient comprising lactose, mannitol, or a mixture thereof. In some embodiments, the macrocyclic lactone comprises ivermectin. In some embodiments, the insect growth regulator comprises cyromazine. In some embodiments, the granule further comprises a water miscible polymeric binder.

In some embodiments according to the first aspect of the invention, the granules comprise about 0.5 to about 3.0% (w/w) of at least one macrocyclic lactone, about 25 to about 75% (w/w) of at least one insect growth regulator, a surfactant excipient comprising about 5 to about 25% (w/w) polysorbate 20, polysorbate 60, polysorbate 65, polysorbate 80, or polysorbate 85, and a diluent excipient comprising lactose, mannitol, or a mixture thereof. In some embodiments, the insect growth regulator comprises cyromazine. In some embodiments, the macrocyclic lactone comprises ivermectin. In some embodiments, the surfactant excipient comprises about 5 to about 25% (w/w) polysorbate 80. In some embodiments, the granule further comprises a water miscible polymeric binder.

In some embodiments, the parasiticidal granule of the invention comprises ivermectin, cyromazine, cetrimide, and a diluent excipient selected from mannitol, lactose, or a mixture thereof. In some embodiments, the parasiticidal granule of the invention consists essentially of ivermectin, cyromazine, cetrimide, a diluent excipient selected from mannitol, lactose, or a mixture thereof, optionally, an antioxidant stabilizer, and optionally, one or more water miscible polymeric binders. In one embodiment, the amount of ivermectin is about 0.5% to about 3.0% (w/w). In certain embodiments, the amount of ivermectin is about 0.5 to about 2.5% (w/w). In certain embodiments, the amount ivermectin is about 0.5 to about 2.0% (w/w). In certain embodiments, the amount ivermectin is about 0.7 to about 1.7% (w/w). In certain embodiments, the amount ivermectin is about 1.0 to about 2.0% (w/w). In one embodiment, the amount of ivermectin is about 1.5% (w/w). In some embodiments, the amount of cyromazine is about 25 to about 75% (w/w). In some embodiments, the amount of cyromazine is about 25 to about 60% (w/w). In some embodiments, the amount of cyromazine is about 25 to about 55% cyromazine, (w/w). In some embodiments, the amount of cyromazine is about 45 to about 55% (w/w). In some embodiments, the amount of cyromazine is about 50% (w/w). In some embodiments, the amount of cetrimide is about 1 to about 20% (w/w). In some embodiments, the amount of cetrimide is about 1 to about 15% (w/w). In some embodiments, the amount of cetrimide is about 1 to about 10% (w/w). In some embodiments, the amount of cetrimide is about 1 to about 5% (w/w). In one embodiment, the amount of cetrimide is about 5% (w/w). In some embodiments, the diluent is either mannitol or lactose. In one embodiment, the diluent is lactose. In one embodiment, the diluent is mannitol. In some embodiments, the invention comprises a polymer excipient that is polyvinylpyrrolidone, hydroxypropylmethylcellulose, or mixtures thereof. In some embodiments, the invention comprises polyvinylpyrrolidone.

In one embodiment according to the invention, the parasiticidal granule comprises about 1.5% (w/w) ivermectin, about 50% (w/w) cyromazine, about 5% (w/w) cetrimide, and mannitol, lactose, or a mixture thereof. In certain embodiments, the amounts of ivermectin, cyromazine, and cetrimide are within plus or minus 20%, plus or minus 10% or plus or minus 5% of the specified amounts (e.g. plus or minus 20%, 10% or 5% of each one of ivermectin (1.5%), cyromazine (50%), and cetrimide (5%)). For example, plus or minus 20% of the specification of 1.5% (w/w) for ivermectin, is about 1.2% ivermectin to about 1.8% ivermectin. In one embodiment, the granule comprises mannitol. In a further embodiment, the granule comprises polyvinylpyrrolidone.

In some embodiments, the parasiticidal granule of the invention comprises ivermectin, cyromazine, polysorbate 80, and a diluent excipient selected from mannitol, lactose, or a mixture thereof. In one embodiment, the amount of ivermectin is about 0.5% to about 3.0% (w/w). In one embodiment, the amount of ivermectin is about 0.5% to about 2.0% (w/w). In certain embodiments, the amount ivermectin is about 0.7 to about 1.7% (w/w). In certain embodiments, the amount of ivermectin is about 1.0 to about 2.0% (w/w). In one embodiment, the amount of ivermectin is about 1.5% (w/w). In some embodiments, the amount of cyromazine is about 25 to about 60% (w/w). In some embodiments, the amount of cyromazine is about 25 to about 75% (w/w). In some embodiments, the amount of cyromazine is about 25 to about 55% (w/w) cyromazine. In some embodiments, the amount of cyromazine is about 45 to about 55% (w/w). In some embodiments, the amount of cyromazine is about 50% (w/w). In some embodiments, the amount of polysorbate 80 is about 5 to about 25% (w/w). In one embodiment, the amount of polysorbate 80 is about 5 to about 15% (w/w). In some embodiments, the amount of polysorbate 80 is about 5 to about 10% (w/w). In some embodiments, the amount of polysorbate 80 is about 7.5% (w/w). In some embodiments, the diluent is either mannitol or lactose. In one embodiment, the diluent is preferably mannitol. In some embodiments, the invention comprises a polymer excipient that is polyvinylpyrrolidone, hydroxypropylmethylcellulose, or mixtures thereof. In certain embodiments, the invention comprises polyvinylpyrrolidone.

In one embodiment according to the invention, the parasiticidal granule comprises about 1.5% ivermectin, about 50% cyromazine, about 7.5 percent polysorbate 80, and either mannitol or lactose. In certain embodiments, the amounts of ivermectin, cyromazine, and polysorbate 80 are within plus or minus 20%, plus or minus 10% or plus or minus 5% of the specified amounts (e.g. plus or minus 20%, 10% or 5% of each one of ivermectin (1.5%), cyromazine (50%), and polysorbate 80 (7.5%)). In one embodiment, the parasiticidal granule according to the invention comprises about 1.5% ivermectin, about 50% cyromazine, about 7.5 percent polysorbate 80, and mannitol. In a further embodiment, the granule comprises polyvinylpyrrolidone. In one embodiment, the parasiticidal granule consists essentially of ivermectin, cyromazine, polysorbate 80, a diluent excipient selected from mannitol, lactose, or a mixture thereof, optionally, an antioxidant stabilizer and optionally, one or more water miscible polymeric binders.

As would be understood by one skilled in the art, any of the embodiments in regard to an amount of one component may be combined with another embodiment in regard to an amount of another component. For example, in one exemplary embodiment the invention provides for a parasiticidal veterinary granules comprising an amount of macrocyclic lactone or ivermectin that is plus or minus 20% of a specification of 1.5% (w/w) macrocyclic lactone or ivermectin, namely about 1.2 to about 1.8% macrocyclic lactone or ivermectin, and in that embodiment, the exemplary granule comprises an amount of insect growth regulator or cyromazine that is plus or minus 10% of a specification of 50% (w/w) of insect growth regulator or cyromazine, namely about 45 to about 55% (w/w) insect growth regulator or cyromazine. The person skilled in the art would therefore readily combine any one or more of the embodiments disclosed herein, and would not consider that any one embodiment was limited to a specific combination.

The invention provides for certain embodiments of a parasiticidal veterinary granule which contain a residual amount of water (i.e. the moisture content), wherein a residual amount of water is an amount less than about 5% (w/w), less than about 4% (w/w), less than about 3% (w/w), and less than about 2.5% (w/w) water.

In another aspect of the invention, a method for treating, controlling, or preventing an ectoparasite infestation and/or an endoparasite infection in an animal is provided which comprises administering to an animal a solution formed by mixing with water a granule according to the first aspect. In one embodiment, the aqueous solution formed with the granule is administered to an animal topically. In one preferred embodiment, the invention provides a method for treating, controlling or preventing fly strike and louse infestations in sheep. In some embodiments, at least 10% efficacy is achieved against the target pest. In some embodiments, at least 20%, at least 30%, at least 40%, at least 50%, at least 60%, at least 70%, at least 80%, at least 90%, at least 95%, at least 98%, or at least 99% efficacy is achieved against the target pest. In some embodiments, efficacy against the target pest is reflected in reduced infection or infestation in a portion of a group or herd of animals, such as reduced occurrence of endoparasite infection or ectoparasite infestation in at least 10%, 20%, 30%, 40%, 50%, 60%, 70%, 80%, 90%, 95%, 98%, or 99% of the group or herd.

In another aspect, the invention provides a method of making a granule according to the first aspect. In one embodiment, the method comprises the steps of:

(i) Dissolving a macrocyclic lactone in a surfactant excipient or dissolving a macrocyclic lactone in an aqueous solution of a surfactant excipient, and, optionally, adding a binder dissolved in water;

(ii) Mixing together an insect growth regulator and a diluent excipient;

(iii) Combining the products from steps (i) and (ii), mixing to form a wet granules mass, optionally, adding a binder; and (iv) Drying the wet granules mass at 50-70° C. until the moisture content is below about 2.5% (w/w).

In a further step, the dried granules according to the invention are sized and packed. In one embodiment, the granules are sized through 20-30 mesh and packed in water soluble bags. Alternative packaging will also be known to one skilled in the art and will depend upon considerations such as shipping and storage conditions.

A fourth aspect of the invention is the use of a granule of the first aspect in the manufacture of a medicament for the therapeutic and/or prophylactic treatment of an animal against an ectoparasite infestation and/or an endoparasite infection.

Definitions

Terms used herein will have their customary meaning in the art unless specified otherwise.

Binders include natural or synthetic water soluble polymers that may be added as solutions, or added dry, as a solid, to a granulation mix. Binders are used to agglutinate components in a composition. Binders that may be used in the compositions of the invention include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders.

Excipient has its customary meaning in the art of pharmaceutical and veterinary medicine formulation, which is a substance that is formulated with an active ingredient. Excipients include anti-adherents, binders, coatings, colors, disintegrants, glidants, lubricants, preservatives, and sorbents. An excipient may be included for a variety of purposes including for the purpose of bulking up a solid formulation, wherein an excipient may be referred to as a bulking agent, a filler, or a diluent. Excipients may also be added to enhance solubility of a solid in a liquid solvent, and they may be used as an aid in the manufacturing process to facilitate powder flowability. Excipients may also be useful for enhancing product stability and shelf life. Commonly used excipients for tableting, such as tableting by wet granulation are diluents (such as microcrystalline cellulose, lactose monohydrate, dibasic calcium phosphate, and mannitol); binders (such as pre-gelatinised starch, povidone, hydroxypropyl cellulose, and hypromellose); disintegrants such as partly pregelatinised starch, sodium starch glycolate, croscarmellose sodium, and crospovidone; lubricants such as magnesium stearate, sodium stearyl fumarate, and mixtures of talc and stearic acid; and glidants, such as colloidal silicon dioxide.

Polymeric excipients contemplated for the instant invention may be natural, semi-synthetic, or synthetic. Binders, such as water miscible binders, are exemplary polymeric excipients. Common polymeric binders are starch, cellulosic ethers such as carboxymethylcellulose and hydroxypropyl cellulose. Poly(vinylpyrrolidone) can be used as a binder. Polymeric excipients also include disintegrating agents which help with rapid disintegration of a solid product (e.g. a tablet or a granule) in water or an aqueous milieu. Pre-gelatinised starch or chemically modified starch, such as sodium starch glycolate are used as disintegrants. Purely synthetic polymers include crosslinked N-vinylpyrrolidone, also called crospovidone which is commercialized under the tradename Polyplasdone®. Polyethlene glycol is an example of a polymeric excipient used as a lubricant.

Macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am.

Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871, 719, 4,874,749, 4,427,663, 4,310,519, 4,199,569, 5,055,596, 4,973,711, 4,978,677, 4,920,148 and EP 0 667 054, all incorporated herein by reference.

For the purpose of this application, the term "stable" or "stability" means that the granule meets or exceeds chemical and physical assay criteria after a period of time. The period of time that the granular product according to the instant invention is stable can also be termed the product "shelf life". In some embodiments, the shelf life may be 3 months, 6 months, or may preferably be 12 months, 18 months, 24 months or more than 24 months. The shelf life may also be expressed as a range such as 18-24 months.

Physical and chemical testing includes testing according to good laboratory practice methods. The methods may be methods developed by and particular to a private laboratory. Accelerated stability testing includes holding a sample at an elevated temperature, such as at 30° C. or at 40° C. for a period of time so as to predict the stability of the product at a temperature that is less than the elevated temperature. Stability may be expressed qualitatively in some cases and quantitatively in others. Physical/chemical testing is well-known in the art and includes testing for a variety of properties that may include, but is not limited to, color, density, viscosity, osmolarity, particle size, loss on drying, optical density (haze), pH, and dissolution.

Stability testing also commonly includes determining the concentration of components in a composition as well as the concentration of degradation products. If stability is expressed as a numerical value, such as the concentration of an ingredient in a composition, then stable means that the concentration of one or more ingredients meets or exceeds a minimum specification. Stability is commonly expressed as a percentage of an amount initially formulated. Stability also may indicate that degradation products of one or more ingredients are less than a specified value. The specification may be expressed as being plus or minus (+/−) a percentage, such as +/− one percent of a concentration or weight, or +/− two percent, +/− five percent, +/− ten percent, or +/− any percent between one and ten percent, or +/− a percent higher than ten percent of a specified concentration or weight.

Wet granulation is a traditional tablet manufacturing process. Wet granulation processes may be described as low shear, high shear, and fluid bed granulation. Typical steps in low shear and high shear processing are: 1) Dry mixing of components, and combining with optional binder solution; 2) Wet granulation using a mixer; 3) Wet screening (optional); 4) Drying; 5) Milling; 6) Blending of extra-granular components and lubrication (optional); and 6) compaction (optional). The final compaction step may be omitted if the product is not a highly compacted product, such as would be the case for soft granules.

The term "parasiticidally effective" as used herein means that the composition is suitable to control the parasite in question to a desired extent such as, for example, at least 50%, at least 60%/a, at least 70%, at least 80%, at least 90%, 95%, 98% or 100% efficacy against a target parasite. In such case, effective means effective in an individual animal, or effective against a portion of a group or herd of animals.

The terms "treating" "therapeutic" or "controlling" are intended to mean the administration of a composition according to the invention, such as administration of a solution formed by mixing a granule according to the invention with water, to an animal that has a parasitic infestation or infection for the eradication of the parasite or the reduction of the parasites infesting or infecting the animal undergoing treatment.

The term "preventing" and "prophylactic" are intended to mean the administration of the composition according to the invention, such as administration of a solution formed by mixing a granule according to the invention with water, to an animal before the parasitic infection or infestation has occurred in order to keep said infection or infestation from occurring.

EXAMPLES

Below, the presently disclosed invention will be described by way of examples, which are provided for illustrative purposes only and accordingly are not to be construed as limiting the invention.

Granule Ingredients

Compositions of granules according to the instant invention were determined by investigation of the effect of various surfactants, diluents, and other excipients.

The solubility of ivermectin was determined in various surfactants including polysorbate 80, PEG 35 castor oil (Cremophor EL), polysorbate 80+PEG 35 castor oil mixture (1:1), polysorbate 65+polysorbate 85, poloxamer 188, benzalkonium chloride (50% Solution), sodium lauryl sulphate (50% Solution), dioctyl sodium sulfosuccinate (DOSS), cetrimide, and lecithin, and the optimal concentrations for selected surfactants, including polysorbate 80 and cetrimide were determined.

Some surfactants are liquid at room temperature (e.g. polysorbate 65, polysorbate 80, polysorbate 85 and PEG 35 castor oil), and ivermectin could be dissolved directly into these surfactants. Other surfactants that are solid (e.g. cetrimide, sodium lauryl sulphate, dioctyl sodium sulfosuccinate poloxmers, benzalkonium chloride, etc) were first dissolved in water at various concentrations depending on their solubility. For instance, sodium lauryl sulfate is quite water soluble and aqueous solutions up to 50% are possible, whereas poloxamers have lower water solubility. In the case of solid surfactants, the solubility of ivermectin was determined in water/surfactant mixtures. Polysorbate 80 and cetrimide aqueous solutions were picked for further development including optimizing the amount of surfactant required to completely solubilize ivermectin and to get granules of adequate physical and chemical stability. Adequate chemical stability means that the amount of the actives and active degradation products are within specification. By adequate physical stability is meant, at least, that the granules have sufficient strength to withstand crumbling during transportation. Transportation stability can be assessed by methods that simulate the forces typically encountered by a product during shipping. Shipping may be simulated in the laboratory, or a product may be actually shipped. After a shipping test, desirable characteristics of the granule such as granule size are evaluated and compared to the control product that was not subjected to shipping stress.

Granules were prepared using 3%, 5%, 7.5%, and 10% cetrimide. When diluted in water, 1:500 (w/v), the 3.0% cetrimide granules yielded a hazy solution, but the dissolution of the granules was acceptable despite the haziness. Granule dissolution was judged as being acceptable if water dissolution happened easily without requiring lengthy (e.g. less than about 10 minutes) mechanical stirring. Mechanical stirring may be done by hand or by motor, such as by a drill motor attached to a stirring shaft. In some cases the required agitation may be provided by a recirculating pump within a supply tank in which the granules of the invention are added prior to application to the animal being treated. In this circumstance, a significant amount of haziness may be acceptable as long as the particle size of any solids is sufficiently small so that they will not block filters and/or valves, etc. Ideally the resulting solution is clear, but slight haziness caused by micron size particles is acceptable. The 5%, 7.5% and 10% cetrimide granules yielded clear solutions when dispersed into water. Granules were also prepared using 7.5% and 15% polysorbate 80.

Solutions of ivermectin were prepared either directly in surfactant (e.g. in case of liquid surfactants) or in aqueous solution of surfactants, and the solutions were adsorbed onto various diluents, including lactose, mannitol, and sugar. Mannitol and lactose in particular gave good results. The mannitol and lactose containing granules were relatively softer and dissolved faster in water.

Super disintegrants such as crospovidone (crosslinked polyvinylpyrrolidone) and croscarmellose (crosslinked sodium carboxymethyl cellulose) were investigated for faster water dissolution of granule formulations. While the dissolution was faster in initial trials, the solutions were hazy due to insoluble particles of disintegrant.

Optimal concentrations of binders such as polyvinylpyrrolidone and hydroxypropyl methylcellulose were also determined for some granule compositions. Desirably, optimal granules should not be too hard or too soft. When granules are too hard, they may be difficult to dissolve; if too soft, they may crumble during transportation and storage.

Table 1 below summarizes representative granules according to some embodiments of the invention.

TABLE 1

| Composition for 1 Kg granules | | |
|---|---|---|
| | | Mass |
| Actives | cyromazine | 500 g |
| | ivermectin | 15 g |
| Surfactant | polysorbate 80 or | 75 g |
| | cetrimide | 50 g |
| Stabilizer | BHT | 0.5 g |
| Binder | PVP K30 or HPMC 0 | 0-10 g |
| Diluent | lactose or mannitol | q.s. to 1000 g |

Granule Manufacturing Process, General Procedure:

Granules according to certain embodiments of the invention were prepared using the following process:

1. Ivermectin and BHT were dissolved in surfactant or aqueous solution of surfactant.
2. Cyromazine and diluent were mixed in the granulator bowl (e.g. planetary mixer or rapid mixer granulator (RMG)).
3. The step 1 solution was transferred to the step 2 mixture, and the combination was mixed to form wet granules mass.
4. Binder, if required was dissolved in water and added. The quantity of water required depends on other excipients
5. The wet granules mass was dried at 50-70° C. until moisture content was below 2.5% (w/w).
6. Dried granules were sized through 20-30 mesh and packed in water soluble bags or other suitable packing such as polyethylene bags, triple laminate bags, and plastic containers.

Table 2 summarizes cyromazine/ivermectin granules prepared using the above granule manufacturing process.

TABLE 2

| Options for 1 Kg granules | | | | | |
|---|---|---|---|---|---|
| | | Option 1 | Option 2 | Option 3 | Option 4 |
| | | Batch No. | | | |
| | | A | B | C | D |
| ACTIVES | cyromazine | 500 g | 500 g | 500 g | 500 g |
| | ivermectin | 15 g | 15 g | 15 g | 15 g |
| Surfactant | | PS80[1] 75 g | cetrimide 50 g | PS80[1] 75 g | cetrimide 50 g |
| Stabilizer | BHT | 0.5 g | 0.5 g | 0.5 g | 0.5 g |
| Binder | PVP[2] | 5 g | — | 5 g | 5 g |
| Diluent | | lactose q.s. to 1 kg | lactose q.s. to 1 kg | mannitol q.s. to 1 kg | mannitol q.s. to 1 kg |
| Water for granulation[3] | | q.s. | q.s. | q.s. | q.s. |

Notes:
[1]PS80: polysorbate 80.
[2]PVP: K30 (povidone or polyvinylpyrolidone).
[3]Options 1 & 3 granule manufacturing methods, step 4 (see below).

The following variations in the general granule manufacturing procedures were used, depending upon the excipients in the granules.

Option 1 and Option 3 Granule Manufacturing Methods
1. Ivermectin and BHT were dissolved in surfactant,
2. Cyromazine and diluent were mixed in the granulator bowl; either a planetary mixer or a Rapid Mixer Granulator (RMG) was used.
3. Step 1 solution was transferred to Step 2 and mixed to form wet granules mass.
4. Binder dissolved in water was added. The quantity of water required depends on other excipient(s), usually around ⅒ of batch size.
5. The wet granules mass were dried at 50-70° C. until the moisture content was below 2.5% (w/w).
6. The dried granules were sized through 20-30 mesh and packed in water soluble bags or other suitable packing.

Option 2 and 4 Granule Manufacturing Methods
1. Cetrimide was dissolved in water.
2. Ivermectin and BHT were dissolved in cetrimide solution from Step 1; binder was added if required (option 4).
3. Cyromazine and diluent were mixed in the granulator bowl; either planetary mixer or Rapid Mixer Granulator (RMG) was used.
4. Step 1 solution was transferred to Step 2 and mixed to form wet granules mass.
5. The wet granules mass was dried at 50-70° C. until the moisture content was below 2.5% (w/w).
6. Dried granules were sized through 20-30 mesh and packed in water soluble bags or other suitable packing.

Stability Studies

The effect of surfactant and diluent excipients on the stability of ivermectin/cyromazine granules was investigated. The stability results for certain granule batches according to the invention are summarized in Table 6.

Cyromazine and ivermectin and degradation products (DPs) in the granules were assayed by reverse-phase C18 HPLC according to in-house developed isocratic methodology as summarized in Table 3. The HPLC system suitability parameters checked for cyromazine and ivermectin are listed in Tables 4 and 5, respectively.

Granule samples were prepared for HPLC assay by first preparing a sample stock solution by adding 550 mg of ground granule sample in about 10 mL of water, and diluting the aqueous mixture to 100.00 mL with methanol. The resulting methanol/water sample stock solution was used for the cyromazine assay. For the ivermectin assay, 2.00 mL of the methanol/water sample stock solution was diluted to 100.00 mL with mobile phase.

TABLE 3

HPLC Assay and Degradation Products for
Cyromazine and Ivermectin in Cyromazine Ivermectin Granules

|  | Cyromazine Assay 061 | Ivermectin Assay 060 |
| --- | --- | --- |
| Chromatographic System |  |  |
| Column Dimensions Particle Size Column Part No. | Kinetex ® C18 100 Å 150 mm × 4.6 mm 5 micron 00F-4601-E0 (Phenomenex, USA) | InertSustainSwift C18 150 mm × 4.6 mm 3 micron 5020-88149 (GL Sciences, Japan) |
| Wavelength | 214 nm | 245 nm |

TABLE 3-continued

HPLC Assay and Degradation Products for
Cyromazine and Ivermectin in Cyromazine Ivermectin Granules

|  | Cyromazine Assay 061 | Ivermectin Assay 060 |
| --- | --- | --- |
| Flow Rate | 1.8 mL/min | 1.5 mL/min |
| Column Temperature | 40° C. | 40° C. |
| Run Time: | 7 minutes | 20 minutes |
| Injection Volume | 10 µL | 20 µL |
| Mobile Phase | Water:Methanol:Acetonitrile 93:5:2 (v/v); (3.72 g $K_2HPO_4$, 6.48 g $KH_2PO_4$)/liter mobile phase | Acetonitrile:Methanol: Water 106:55:39, (v/v) |
| Standard | 0.0550 mg cyromazine/mL, prepared as follows: Std Stock: 55 mg* cyromazine standard in 100.00 mL methanol. Further dilute 5 mL std stock to 50.00 mL w/mobile phase (*account for purity in calculating weight of cyromazine) | 0.08 mg ivermectin/mL, prepared as follows: Std Stock: 40 mg Ivermectin/50.00 mL methanol. Further dilute 5 mL std stock to 50.00 mL w/methanol. |

TABLE 4

Cyromazine HPLC Assay System Suitability Parameters

| Name | Retention time (min) | Asymmetry | Theoretical plates |
| --- | --- | --- | --- |
| Cyromazine | 2.8 ± 1 min | NMT 2.0 | NLT 5000 |

TABLE 5

Ivermectin HPLC Assay System Suitability Parameters

| Name | Retention time (min) | Asymmetry | Theoretical Plates | Resolution (Between Ivermectin B1a and B1b) |
| --- | --- | --- | --- | --- |
| Ivermectin B1b | 6.6 ± 1 min | N/A | N/A | NLT 3.0 |
| Ivermectin B1a | 8.2 ± 1 min | NMT 2.0 | NLT 3000 |  |

The Australian regulatory acceptance level for the ivermectin and cyromazine degradation products is 2.7% (w/w), according to the VICH GL11R (Quality) Guideline implemented in 2008. 30° C. is the temperature for real time stability study for Australia. Therefore 30° C./6 month is equivalent to 6 months shelf life in Australia. 40° C. is an accelerated condition; therefore 40° C./6 Months may be equivalent to 18-24 months shelf life and 40° C./12 months may be equivalent to 36-48 months shelf life.

Tables 6A and 6B show the effect of the surfactants, polysorbate (Tween 80) and cetrimide, and the diluents, lactose and mannitol, on ivermectin and cyromazine stability. The composition of granule batches A-D in Tables 6A and 6B is listed in Table 2.

TABLE 6A

Effect of Surfactant and Diluent on Ivermectin Stability

|  | Ivermectin (% of initial) | | | |
| --- | --- | --- | --- | --- |
| Stability Condition Time (months "M")-Temp. | Batch A Tween 80, Lactose | Batch B Cetrimide, Lactose | Batch C Tween 80, Mannitol | Batch D Cetrimide, Mannitol |
| Initial | 100.0 | 100.0 | 100.0 | 100.0 |
| 3M-30° C. | 97.4 | 97.8 | 97.2 | 98.7 |

TABLE 6A-continued

Effect of Surfactant and Diluent on Ivermectin Stability

| Stability Condition Time (months "M")-Temp. | Batch A Tween 80, Lactose | Batch B Cetrimide, Lactose | Batch C Tween 80, Mannitol | Batch D Cetrimide, Mannitol |
| --- | --- | --- | --- | --- |
| 6M-30° C. | 96.9 | 99.5 | 98.9 | 100.0 |
| 9M-30° C. | 96.7 | 97.8 | 97.9 | 99.2 |
| 12M-30° C. | 95.5 | 98.9 | 98.6 | 99.5 |
| 3M-40° C. | 95.3 | 98.2 | 95.8 | 98.7 |
| 6M-40° C. | 92.2 | 96.9 | 93.8 | 99.6 |
| 9M-40° C. | 90.7 | 94.7 | 94.6 | 99.0 |
| 12M-40° C. | 87.7 | 92.8 | 94.9 | 99.0 |

TABLE 6B

Effect of Surfactant and Diluent on Cyromazine Stability

| Stability Condition Time (months "M")-Temp. | Batch A Tween 80, Lactose | Batch B Cetrimide, Lactose | Batch C Tween 80, Mannitol | Batch D Cetrimide, Mannitol |
| --- | --- | --- | --- | --- |
| Initial | 100.0 | 100.0 | 100.0 | 100.0 |
| 3M-30° C. | 99.7 | 99.9 | 99.0 | 99.5 |
| 6M-30° C. | 99.6 | 100.0 | 99.7 | 98.8 |
| 9M-30° C. | 99.1 | 100.0 | 99.6 | 99.4 |
| 12M-30° C. | 99.0 | 100.5 | 99.5 | 100.1 |
| 3M-40° C. | 100.0 | 99.6 | 100.1 | 99.5 |
| 6M-40° C. | 100.1 | 99.9 | 99.8 | 99.6 |
| 9M-40° C. | 99.6 | 100.1 | 100.0 | 99.6 |
| 12M-40° C. | 98.6 | 99.9 | 100.1 | 99.9 |

As shown in Table 6A all of the granules retained at least 95% of the initial amount of ivermectin after 12 months at 30° C., with the percent ivermectin being higher in the cetrimide granules (Batches B and D) compared to the polysorbate 80 granules (Batches A and C). Furthermore, after 12 months at 40° C., the cetrimide plus mannitol granules (Batch D) retained 99% ivermectin, which is predictive of three (3) to four (4) years shelf life under standard (i.e. 30° C. storage) conditions. Cyromazine was at least 99% of the initial amount for all batches at all storage times (up to 12 months), at 30° C. as well as at 40° C.

The stability of the ivermectin/cyromazine granules as evidenced in Tables 6A and 6B is surprising and unexpected.

The invention is further described in the following numbered paragraphs:

1. A parasiticidal veterinary granule comprising
   (a) at least one macrocyclic lactone compound;
   (b) at least one insect growth regulator (IGR);
   (c) at least one surfactant excipient; and
   (d) at least one diluent excipient,
wherein said granule remains stable and pharmaceutically active for at least 6 months, and said granule, when mixed in water, forms a parasiticidally effective liquid composition.

2. The granule according to paragraph 1 wherein the IGR is selected from the group consisting of cyromazine, dicyclanil, diflubenzuron, fluazuron, formamidines, hydroprene, lufenuron, methoprene, novaluron, pyriproxyfen, triflumuron, and mixtures thereof.

3. The granule according to paragraph 2 wherein the IGR comprises cyromazine, dicyclanil, or a combination thereof.

4. The granule according to paragraph 3 wherein the IGR comprises cyromazine.

5. The granule according to paragraph 4 wherein the amount of cyromazine is about 25 to about 75% (w/w).

6. The granule according to paragraphs 1 or 5, wherein the amount of macrocyclic lactone is about 0.5 to about 3.0% (w/w).

7. The granule according to paragraph 6, wherein the at least one macrocyclic lactone compound comprises ivermectin.

8. The granule according to paragraph 1, wherein the at least one surfactant excipient comprises at least one quaternary ammonium compound.

9. The granule according to paragraph 8, wherein the surfactant excipient comprises about 1 to about 20% (w/w) cetrimide.

10. The granule according to paragraph 1, wherein the surfactant excipient comprises about 5 to about 25% (w/w) of a polysorbate selected from polysorbate 20, polysorbate 60, polysorbate 65, polysorbate 80, polysorbate 85, and mixtures thereof.

11. The granule according to paragraph 1, wherein the diluent excipient comprises a water soluble sugar selected from lactose, mannitol, and mixtures thereof.

12. The granule according to paragraph 1, further comprising at least one polymer excipient.

13. The granule according to paragraph 12, wherein the polymer excipient comprises one or more water miscible binders selected from polyvinylpyrrolidone, hydroxypropylmethylcellulose, and mixtures thereof.

14. The granule according to paragraph 1, further comprising an antioxidant stabilizer selected from butylated hydroxytoluene (BHT), butylated hydroxyanisole (BHA), sodium metabisulphite, tocopherol, tocopherol derivatives, propyl gallate, and mixtures thereof.

15. The granule according to paragraph 14, wherein the stabilizer is butylated hydroxytoluene (BHT).

16. The granule according to paragraph 1, wherein at least 99% of the formulated amount of insect growth regulator and at least 95% of the formulated amount of macrocyclic lactone is retained for at least 12 months at 30° C., 40° C., or at 30° C. and at 40° C.

17. A parasiticidal veterinary granule comprising
   (a) ivermectin;
   (b) cyromazine;
   (c) at least one surfactant excipient; and
   (d) at least one diluent excipient selected from lactose, mannitol, and mixtures thereof,
wherein said granule remains stable and pharmaceutically active for at least 6 months, and said granule, when mixed in water, forms a parasiticidally effective liquid composition.

18. The granule according to paragraph 17, wherein the surfactant excipient comprises about 1 to about 20% (w/w) cetrimide or about 5 to about 25% (w/w) of a polysorbate selected from polysorbate 20, polysorbate 60, polysorbate 65, polysorbate 80, and polysorbate 85, and mixtures thereof.

19. The granule according to paragraph 17 further comprising one or more water miscible polymeric binders selected from polyvinylpyrrolidone, hydroxypropylmethylcellulose, and mixtures thereof.

20. The granule according to paragraph 17 further comprising an antioxidant stabilizer selected from butylated hydroxytoluene (BHT), butylated hydroxyanisole (BHA), sodium metabisulphite, tocopherol, tocopherol derivatives, propyl gallate, and mixtures thereof.

21. The granule according to paragraph 17 wherein the amount of cyromazine is about 25 to about 75% (w/w).

22. The granule according to paragraph 21 wherein the amount of cyromazine is about 50% (w/w).

23. The granule according to paragraph 17 or paragraph 21 wherein the amount of ivermectin is about 0.5 to about 3.0% (w/w).

24. The granule according to paragraph 23 wherein the amount of ivermectin is about 1.5% (w/w).

25. The granule according to paragraph 17 or paragraph 23 wherein at least 99% of the formulated amount of cyromazine and at least 95% of the formulated amount of ivermectin is retained for at least 12 months at 30° C., 40° C., or at 30° C. and 40° C.

26. The granule according to paragraphs 1 or 17 wherein the granule remains stable and pharmaceutically active for at least 2 years.

27. The granule according to paragraph 26, wherein the granule remains stable and pharmaceutically active for at least 3 years.

28. A method of treating, controlling or preventing an ectoparasite and/or an endoparasite infestation in an animal comprising administering to said animal a solution formed by mixing with water a granule according to paragraphs 1 or 17.

29. The method according to paragraph 28 wherein said solution is administered topically.

30. A method of treating, controlling, or preventing fly strike or louse infestation (*Bovicola ovis*) in sheep comprising administering to said sheep a solution formed by mixing with water a granule according to paragraphs 1 or 17.

31. A method of making a granule according to paragraph 1 comprising the steps of:
   (i) Dissolving a macrocyclic lactone in a surfactant excipient or dissolving a macrocyclic lactone in an aqueous solution of a surfactant excipient, and, optionally, adding a binder dissolved in water;
   (ii) Mixing together an insect growth regulator and a diluent excipient;
   (iii) Combining the products from steps (i) and (ii), mixing to form a wet granules mass, optionally, adding a binder; and
   (iv) Drying the wet granules mass at 50-70° C. until the moisture content is below about 2.5% (w/w).

32. Use of a granule according to paragraphs 1 or 17 in the manufacture of a medicament for the therapeutic and/or prophylactic treatment of an animal against an ectoparasite infestation and/or an endoparasite infection.

What is claimed is:

1. A parasiticidal veterinary granule consisting of
   (a) about 1.2 to about 1.8% (w/w) ivermectin;
   (b) about 40 to about 60% (w/w) cyromazine;
   (c) about 4 to about 6% cetrimide (w/w);
   (d) an antioxidant stabilizer;
   (e) a diluent excipient selected from lactose and mannitol; and
   (f) water;
wherein the water content of said granule is below 2.5% (w/w); at least 87% of the formulated amount of ivermectin and at least 95% of the formulation amount of cyromazine are retained when said granule is stored at 30° C., at 40° C., or at 30° C. and at 40° C. for at least 6 months; and said granule, when mixed in water, forms a parasiticidally effective liquid composition.

2. The granule of claim 1 wherein the concentration of cyromazine is about 50% (w/w).

3. The granule of claim 1 or 2, wherein the concentration of ivermectin is about 1.5% (w/w).

4. The granule of claim 1, wherein the cetrimide concentration is about 5% (w/w).

5. The granule of claim 1, wherein the diluent excipient is mannitol.

6. The granule of claim 1, further comprising an antioxidant stabilizer selected from butylated hydroxytoluene (BHT), butylated hydroxyanisole (BHA), sodium metabisulphite, tocopherol derivatives, propyl gallate, and mixtures thereof.

7. The granule of claim 6, wherein the stabilizer is butylated hydroxytoluene (BHT).

8. The granule of claim 1, wherein at least 99% of the formulated amount of cyromazine and at least 95% of the formulated amount of ivermectin is retained for at least 12 months when the granule is stored at 30° C., 40° C., or at 30° C. and at 40° C.

9. A parasiticidal veterinary granule consisting of
   (a) about 1.5% (w/w) ivermectin;
   (b) about 50% (w/w) cyromazine;
   (c) about 5% cetrimide;
   (d) mannitol;
   (e) an antioxidant stabilizer;
   (f) water; and
   (g) optionally, a PVP binder,
wherein the water content of said granule is below 2.5% (w/w); at least 87% of the formulated amount of ivermectin and at least 95% of the formulated amount of cyromazine are retained when said granule is stored at 30° C., at 40° C., or at 30° C. and at 40° C. for at least 6 months, and said granule, when mixed in water, forms a parasiticidally effective liquid composition.

10. The granule of claim 9 further comprising an antioxidant stabilizer selected from BHT, BHA, sodium metabisulphite, tocopherol derivatives, and propyl gallate.

11. The granule of claim 9, wherein at least 99% of the formulated amount of cyromazine and at least 95% of the formulated amount of ivermectin is retained for at least 12 months when the granule is stored at 30° C., 40° C., or at 30° C. and at 40° C.

12. The granule of claim 1 or 9 wherein the granule remains stable and pharmaceutically active for at least 2 years.

13. The granule of claim 12, wherein the granule remains stable and pharmaceutically active for at least 3 years.

14. A method of treating, controlling or preventing an ectoparasite infestation and/or an endoparasite infection in an animal comprising administering to said animal a solution formed by mixing with water a granule according to claim 1 or 9.

15. The method according to claim 14 wherein said solution is administered topically.

16. A method of treating, controlling, or preventing fly strike or louse infestation (*Bovicola ovis*) in sheep comprising administering to said sheep a solution formed by mixing with water a granule according to claim 1 or 9.

* * * * *